(12) United States Patent
Yamamoto et al.

(10) Patent No.: US 10,087,137 B2
(45) Date of Patent: Oct. 2, 2018

(54) CROSS METATHESIS APPROACH TO C11-C13 FATTY-CHAIN AMINO ESTERS FROM OLEIC ACID DERIVATIVES

(71) Applicant: The University of Toledo, Toledo, OH (US)

(72) Inventors: Kana Yamamoto, Toledo, OH (US); Sridhar Viamajala, Toledo, OH (US); Sasidhar Varanasi, Toledo, OH (US); Kim Nguyen, Toledo, OH (US); Godwin Abel, Toledo, OH (US); Ajith Yapa Mudiyanselage, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/320,802

(22) PCT Filed: Jun. 22, 2015

(86) PCT No.: PCT/US2015/036944
§ 371 (c)(1),
(2) Date: Dec. 21, 2016

(87) PCT Pub. No.: WO2015/200200
PCT Pub. Date: Dec. 30, 2015

(65) Prior Publication Data
US 2017/0204051 A1  Jul. 20, 2017

Related U.S. Application Data

(60) Provisional application No. 62/015,869, filed on Jun. 23, 2014.

(51) Int. Cl.
C07C 227/04 (2006.01)
C07C 253/30 (2006.01)
C07C 67/303 (2006.01)
C07C 67/333 (2006.01)
C07C 229/08 (2006.01)

(52) U.S. Cl.
CPC .......... *C07C 227/04* (2013.01); *C07C 67/303* (2013.01); *C07C 67/333* (2013.01); *C07C 229/08* (2013.01); *C07C 253/30* (2013.01)

(58) Field of Classification Search
CPC ... C07C 227/04; C07C 229/08; C07C 253/03; C07C 67/303; C07C 67/333
See application file for complete search history.

(56) References Cited

U.S. PATENT DOCUMENTS

2010/0168453 A1* 7/2010 Dubois ................. C07C 227/04
554/114
2015/0057461 A1* 2/2015 Park ....................... C12N 15/52
554/219

FOREIGN PATENT DOCUMENTS

KR      20110072830      *  6/2011
WO      WO2013/136111   *  9/2013
WO      WO2013151393    * 10/2013

OTHER PUBLICATIONS

Hoveyda et al., "Synthesis of Unsaturated Amino Alcohols through Unexpectedly Selective Ru-Catalyzed Cross-Metathesis Reactions," Organic Letters, 2005, vol. 7, No. 11, 2113-2116.*
Balcar et al., "Hoveyda—Grubbs type metathesis catalyst immobilized on mesoporous molecular sieves MCM-41 and SBA-15," Beilstein J. Org. Chem. 2011, 7, 22-28.*
Hong et al., "Prevention of Undesirable Isomerization during Olefin Metathesis," J. Am. Chem. Soc., 2005, 127 (49), pp. 17160-17161.*
Miao et al., "Tandem Catalytic Acrylonitrile Cross-Metathesis and Hydrogen of Nitriles with Ruthenium Catalysts: Direct Acess to Linear alph, omega-aminoesters from Renewables," ChemSusChem, 2012, 5, 1410-1414.*
English translation of KR20110072830, Jun. 29, 2011, pp. 1-8.*
Brown et al., "The Reaction of Organoboranes with Chloramine and with Hydroxylamine-O-sulfonic Acid. A Convenient Synthesis of Amines from Olefins via Hydroboration," J. Am. Chem. Soc., 1964, 86 (17), pp. 3565-3566 (Year: 1964).*

* cited by examiner

*Primary Examiner* — Pancham Bakshi
*Assistant Examiner* — Mark R Luderer
(74) *Attorney, Agent, or Firm* — MacMillan, Sobanski & Todd, LLC

(57) ABSTRACT

A concise method of producing nylon 11, 12, or 13 precursors from oleic acid or an ester of oleic acid is described. The method involves cross-metathesis reactions as the key C—C bond formation step. Subsequent steps are provided to convert the metathesis product to the corresponding nylon precursors. Also provided are the products of the method.

24 Claims, 13 Drawing Sheets
(12 of 13 Drawing Sheet(s) Filed in Color)

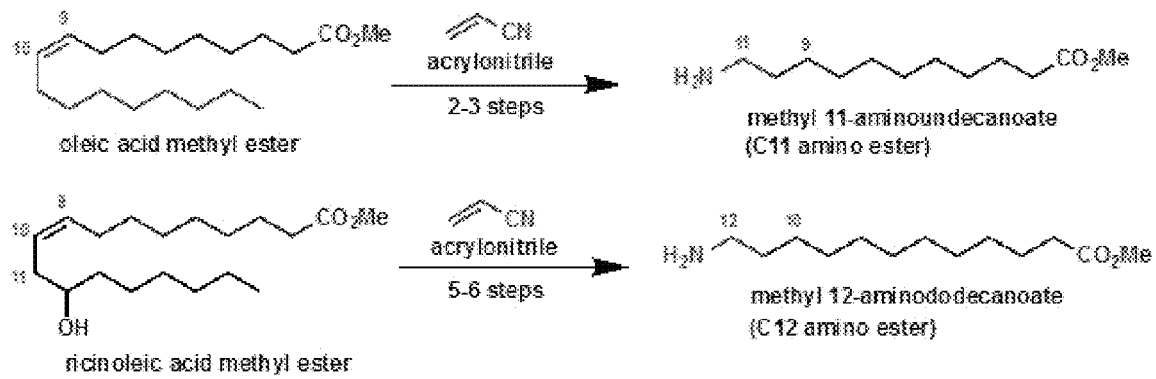
PRIOR ART FIG. 1A
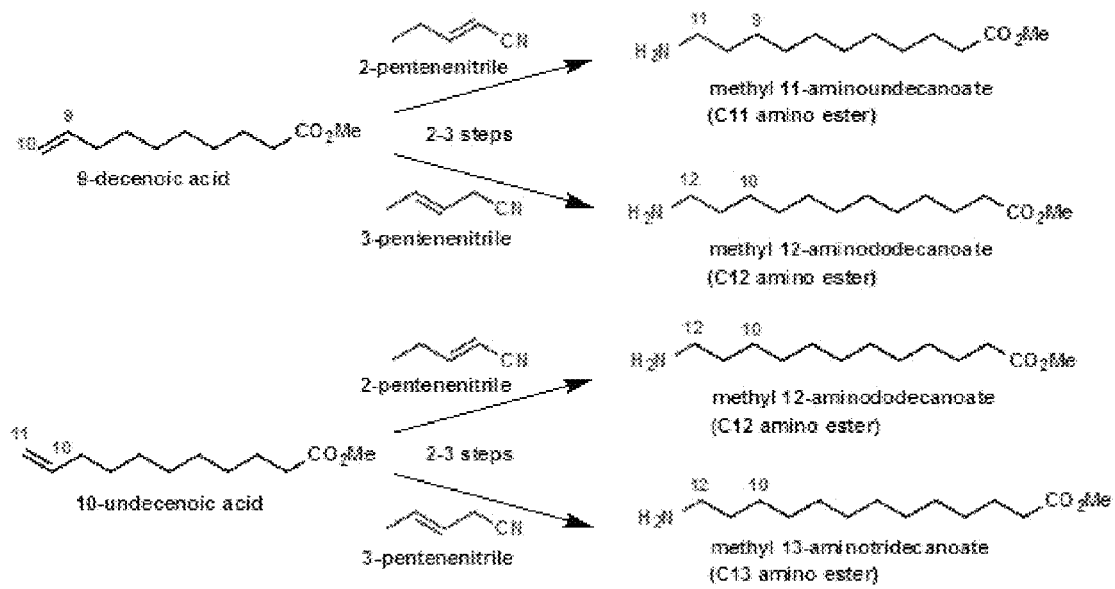
PRIOR ART FIG. 1B

| Entry | Additive[a] (mol%) | Catalyst (mol%) | Temperature (°C) | Reaction time (h) | Conversion (%) | GC area% A | GC area% dimers | dimers/A |
|---|---|---|---|---|---|---|---|---|
| 1[b] | / | 1 | 95 | 21 | 94.7 | 25.5 | 35.8 | 1.404 |
| 2 | / | 1 | 95 | 8 | 92.2* | 28.2 | 21.7 | 0.770 |
| 3 | / | 1 | 80 | 17 | 6.9 | 6.1 | 0 | 0.000 |
| 4 | BQ(10) | 1 | 95 | 5 | 78.7* | 52 | 7.8 | 0.150 |
| 5 | BQ(10) | 2 | 95 | 4 | 92.2 | 49.2 | 17.0 | 0.346 |
| 6 | AA(10) | 2 | 95 | 6 | 48.1 | 20.7 | 4.5 | 0.217 |
| 7 | BQ(10) | 2 | 110 | 6 | 84.4 | 56.4 | 9.0 | 0.160 |
| 8[c] | BQ(10) | 2 | 95 | 6 | 42.7 | 23.5 | 7.8 | 0.332 |
| 9[d] | BQ(10) | 2 | 95 | 6 | 49.1 | 27.8 | 3.3 | 0.119 |
| 10[e] | BQ(10) | 2 | 110 | 4 | 93.8 | 44.2 | 11.1 | 0.251 |
| 11[f] | BQ(10) | 2 | 95 | 6 | 64.6 | 39.2 | 11.0 | 0.281 |
| 12[g] | BQ(10) | 2 | 110 | 6 | 37.7 | 16.9 | 4.0 | 0.237 |
| 13[e] | BQ(50) | 2 | 110 | 4 | 84.7 | 42.2 | 3.0 | 0.071 |
| 14 | BQ(50) | 2 | 110 | 4 | 78.8 | 58.3 | 5.5 | 0.094 |

[b] 2 equiv. of allyl cyanide was used. [c] The catalyst added in one portion. [d] 0.5mL of solvent was used for catalyst delivery; no other solvent was used. [e] 10 equiv. of allyl cyanide was used. [f] 12 mL (11mL + 1mL) of solvent for the whole reaction was used instead of 3mL (2mL + 1mL). [g] Grubbs 2nd generation catalyst was used. [h] BQ: Benzoquinone; AA: Acetic acid.
* denotes approximate values.

FIG. 7 – Table 1

| Entry | Solvent | Reaction time (h) | Conversion (%) | GC area% A | GC area% Dimers | starting material/A | dimers/A |
|---|---|---|---|---|---|---|---|
| 1 | Toluene | 4 | 78.8 | 58.3 | 5.5 | 0.343 | 0.094 |
| 2 | Dichloroethane | 8 | 41.2 | 17.8 | 11.6 | 3.101 | 0.652 |
| 3 | Chloropentafluorobenzene | 2 | 95.3 | 60.1 | 20.6 | 0.075 | 0.343 |
| 4 | Chlorobenzene | 2 | 90.3 | 62.6 | 13.8 | 0.157 | 0.220 |
| 5 | Octafluorotoluene | 5 | 77.2 | 18.62 | 46.0 | 1.176 | 2.470 |
| 6[b] | Chlorobenzene | 3 | 94.9 | 36.3 | 48.5 | 0.146 | 1.336 |
| 7[c] | Chlorobenzene | 1 | 30.7 | 22.3 | 0.5 | 2.861 | 0.022 |
| 8[d] | Chlorobenzene | 3 | 93.5 (77)[e] | 71.2 | 4.1 | 0.091 | 0.058 |

[b] Identical reaction conditions except methyl oleate in chlorobenzene (1 mL) was added dropwise over 1h with the catalyst.
[c] Reaction mixture heated by microwave without dropwise addition of the catalyst. [d] 4.5 mol% of the catalyst was used.
[d] GC yield (Yield quantified by GC).

FIG. 8 – Table 2

| Entry | Reaction time (hrs) | Time of catalyst addition (h) | Conversion (%) | starting material/A | dimers/A | D/A |
|---|---|---|---|---|---|---|
| 1 | 3 | 1 | 82.4 | 0.257 | 0.071 | 0.320 |
| 2[b] | 3 | 1 | 74.6 | 0.777 | 0.103 | 0.454 |
| 3 | 4 | 2 | 88.6 | 0.204 | 0.095 | 0.164 |
| 4 | 4 | 3 | 85.7 | 0.279 | 0.105 | 0.236 |
| 5[c] | 4 | 2 | 44.1 | 3.676 | 0.000 | 0.617 |
| 6[d] | 3 | 2 | 86.3 (56)[f] | 0.303 | 0.151 | 0.156 |
| 7[e] | 4 | 2 | 90.1 | 0.226 | 0.083 | 0.264 |

[b] Reaction temperature was 95 °C.
[c] 10 equiv. of allyl cyanide was used.
[d] 4.5 mol% of catalyst was used.
[e] 3 mol% of catalyst was used.
[f] GC yield (Yield quantified by GC).

FIG. 9 – Table 3

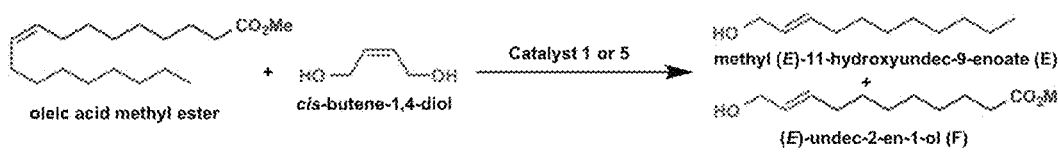

| Entry | Solvent | Catalyst (mol %) | Reaction time (h) | Temperature (°C) | GC Conv. (%) | Starting material/E | dimers/E | F/E |
|---|---|---|---|---|---|---|---|---|
| 1 | PhCl | 1(2) | 7 | 40 | 76 | 0.89 | 0.27 | 1.09 |
| 2 | PhCl | 1(2) | 3.5 | 110 | 9 | 61.48 | - | - |
| 3 | THF | 1(2) | 8 | RT | 30 | 5.36 | 0.37 | 1.18 |
| 4 | DMC | 1(2) | 4 | RT | 66 | 1.35 | 0.39 | 1.08 |
| 5 | EtOAc | 1(2) | 1.5 | 40 | 40 | 6.55 | - | 1.11 |
| 6 | EtOAc | 1(2) | 3 | RT | 78 | 2.81 | 0.23 | 1.09 |
| 7 | EtOAc | 1(2) | 5 | 0 | 92 | 0.22 | 0.18 | 1.14 |
| 8 | EtOAc | 1(2) | 5.5 | 0 | 91(84)[b] | 0.24 | 0.30 | 1.15 |
| 9 | - | 1(2) | 24 | 0 | 54 | 3.14 | 1.97 | 0.77 |
| 10 | EtOAc | 5(2) | 22 | 0 | 91 | 0.23 | 0.21 | 1.22 |
| 11 | EtOAc | 5(1) | 22 | 0 | 91(76)[b] | 0.26 | 0.24 | 1.18 |
| 12 | EtOAc | 5(0.25) | 24 | 0 | 85(63)[b] | 0.43 | 0.39 | 1.09 |

[a] Reaction conditions: To a flask containing methyl oleate (1 eq) and cis-butene-1,4-diol (5 eq) in solvent was added a solution containing the catalyst drop-wise with continuous stirring at the indicated temperature. Reactions conducted at 0 °C was warmed to room temperature after being kept at 0 °C for more than three hours. [b] Isolated yield.

FIG. 10 – Table 4

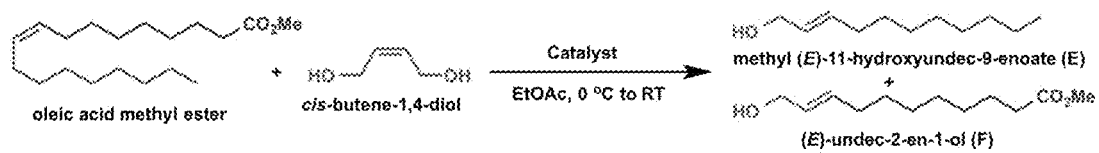

| Entry | Catalyst | Reaction time (h) | GC Conversion (%) | Starting material/E | dimers/E | F/E |
|---|---|---|---|---|---|---|
| 1 | 1 | 5 | 92 | 0.22 | 0.18 | 1.14 |
| 2 | 3 | 3 | 81 | 0.52 | 0.22 | 1.04 |
| 3 | 4 | 3 | 84 | 0.47 | 0.20 | 1.11 |
| 4 | 5 | 24 | 93 | 0.18 | 0.17 | 1.06 |
| 5 | 6 | 48 | 45 | 2.87 | 0.29 | 1.09 |
| 6 | 7 | 16 | 66 | 1.42 | 0.41 | 1.21 |
| 7 | 8 | 5 | 71 | 1.00 | 0.28 | 1.07 |
| 8 | 9 | 5 | 28 | 5.99 | 0.12 | 1.09 |
| 9 | 10 | 8 | 35 | 4.85 | 0.31 | 1.12 |
| 10 | 11 | 24 | 59 | 2.14 | 0.33 | 1.05 |
| 11 | 12 | 23 | 0 | - | - | - |
| 12 | 13 | 24 | 0 | - | - | - |
| 13 | 14 | 24 | 25 | 7.12 | 0.26 | 1.11 |

[a] Reaction conditions: To a flask containing methyl oleate (0.1 mmol) and cis-butene-1,4-diol (0.5 mmol) in ethyl acetate (1 mL) was added a catalyst drop-wise (2 mol%) in ethyl acetate (1 mL) at 0 °C. Reaction mixture was stirred at this temperature for more than 3 hours and warmed to room temperature with continued stirring for additional several hours.

FIG. 11 – Table 5

Methyl 11-cyano-9-undecenoate (A) → Methyl 12-aminododecanoate (B) + Methyl 11-cyanoundecanoate (C)

| Entry | Catalyst amount (mol %) | Amount of t-BuOK (mol %) | Pressure (Bar) | Reaction time (hrs) | GC area (%) B | GC area (%) C | By products |
|---|---|---|---|---|---|---|---|
| 1 | 1 | 15 | 20 | 20 | 1.4 | 71.6 | 15.4 |
| 2 | 3 | 15 | 25 | 20[c] | 6.8 | 55.6 | 29.6 |
| 3[b] | 3+3 | 15 | 25 | 40 | 2.7 | 16.5 | 56.7 |
| 4 | 3 | 30 | 25 | 20[c] | 56.8 | 4.1 | 27.0 |
| 5[b] | 2.5 | 30 | 30 | 20 | 84.9 | 0.5 | 6.8 |
| 6[b] | 3+3 | 30 | 25 | 40 | 22.4 | 15.2 | 48.0 |

[b] Catalyst added in twice, at the beginning and after 20 h.
[c] Hoveyda-Grubbs 2nd generation catalyst was used.
[d] Reaction was kept for 40 h but the results were the same.

FIG. 12 – Table 6

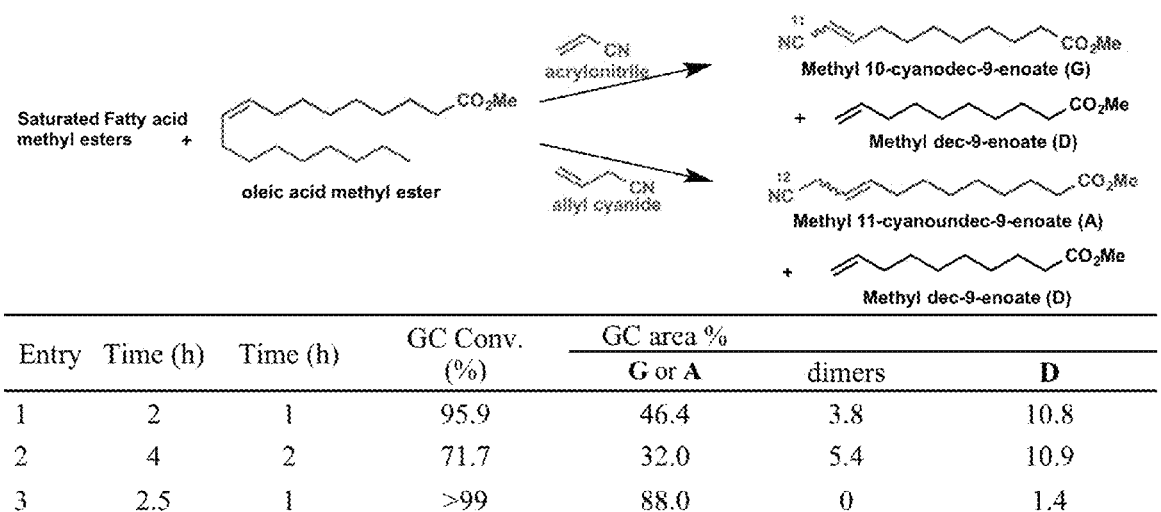
FIG. 13 – Table 7

CROSS METATHESIS APPROACH TO C11-C13 FATTY-CHAIN AMINO ESTERS FROM OLEIC ACID DERIVATIVES

RELATED APPLICATIONS

This application claims priority to U.S. Provisional Application Ser. No. 62/015,869 filed under 35 U.S.C. § 111(b) on Jun. 23, 2014, the disclosure of which is incorporated herein by reference in its entirety.

STATEMENT REGARDING FEDERALLY SPONSORED RESEARCH

This invention was made with government support under Grant Number CHE-1230609 awarded by the National Science Foundation and Grant Number DE-EE0005993 awarded by the United States Department of Energy. The government has certain rights in this invention.

BACKGROUND OF THE INVENTION

Nylon is a series of polymers with a general formula —[$(CH_2)_n$—CONH]— or —[$(CH_2)_n$—CONH—$(CH_2)_m$—NHCO]—, typically named with the length of the methylene units separating the amide functions. Some such examples are nylon 6, nylon 6-6, nylon 7, nylon 8, nylon 9, nylon 11, nylon 12, and nylon 13. Certain nylons, such as nylons 11 and 12, possess excellent chemical resistance, thermal resistance, cold impact resistance, flexibility, and durability. There are many industrial applications of these nylons, including automotive applications, sports applications, medical applications, high-performance cables, electronics, electrical materials, and lenses for glasses. Currently, about 100,000 metric tons of nylon 11 and nylon 12 are produced annually. The use of these nylons in the automotive/transportation industry is increasing at an annual rate of 33.7%, extrapolated to 250,000 metric tons by 2016. Similarly, their use in photovoltaic panels is expected to increase at an annual rate of 36.1% through 2016, and in other general applications is predicted to increase at a rate of 25.3% annually through 2016. Nylon 13 has analogous characteristics to nylon 12 and may be used in similar applications as nylon 12.

Nylon 11, 12, and 13 can be produced from amino acids or their derivatives such as esters or lactams. Currently, the main supply source of C12 amino acid (in lactam form) is produced from petroleum-derived butadiene in a six-step process. While the carbon backbone can be obtained from petrochemical sources by chemical synthesis, there is an increasing interest in the use of renewable resources for the production of this and similar amino acids (and their derivatives), due to growing environmental and sustainability concerns.

Nylon precursor synthesis approaches that use natural fatty acids and esters from plant- or algae-derived biomass as the starting materials are especially attractive methods for producing nylon precursors. Among the natural fatty acids, oleic acid is the predominant component of lipids in most vegetable oils (e.g. soy oil) and algae. While pathways for producing nylon 11 from oleic acid are known, the methods currently used are unsuitable for producing nylon 12 or nylon 13 from the abundantly-available oleic acid. This, in large part, is because of the formation of undesirable isomers produced in the key step, resulting in low overall yields when existing art is applied to produce C12 and C13 amino acids from oleic acid. Accordingly, the methods currently used require more exotic fatty acids to produce nylons 12 and 13. For example, recinoleic acid from castor oil is used to produce C11 and C12 amino acids and esters, while erucic or lesquerolic acid is used to produce a C13 lactam (cyclic amide of C13 amino acid). In one method, erucic acid is first oxidized to produce brassylic acid (a diacid with 13 carbons), which is subsequently converted, over several steps, into a C13 lactam. The lactam can be polymerized to nylon 13. In another method, caster oil is converted to 11-aminoundencanoic acid (C11 amino acid) by a process that begins with base-catalyzed methanolysis of castor oil, which generates methyl recinoleate. The recinoleate is then subjected to a retro-prins reaction to obtain heptanaldehyde and methyl undecyleate. After separation, the latter is hydrolyzed to acid, followed by conversion to an ω-bromo acid by hydrobromination. Finally, the bromine is replaced by an amine over 5-6 steps to produce 11-aminoundecanoic acid.

In a similar approach to produce 11-aminoundecanoic acid from oleic acid, oleic acid or ester is first converted to α-ω-diacid or diester by either homometathesis or enzymatic conversion. After separation and recovery of the diacid or diester from the reaction mixture, they are subjected to oxidative cleavage to produce α-ω-formylacids or esters. The aldehyde is converted to an amine by reductive amination in the final step. The process of generating fatty amino acids of other chain lengths (C9 to C15) is possible using a similar method, starting from other natural fatty acids or their derivatives.

Another approach to produce 11-aminoundecanoic acid and 12-aminododecanoic acid from components of castor oil—oleic acid and recinoleic acid—involves subjecting oleic acid or ester to a cross metathesis reaction with acrylonitrile to produce 10-cyano-9-decenoic acid or ester, followed by reduction using high-pressure hydrogenation to remove unsaturation. (PRIOR ART FIG. 1A.) 12-aminododecanoic acid is also prepared in analogous fashion starting from 10-undecenoic acid prepared from pyrolysis of recinoleic acid. (PRIOR ART FIG. 1A.) It has been reported that α-ω-diacids or diesters synthesized by homometathesis or fermentation, or acids or esters with a terminal olefin prepared from ethylenolysis, can also be used as the starting material in lieu of oleic acid.

Another method starts with either 9-decenoic or 10-undecenoic acids or esters (or other ω-terminal fatty acids with various chain lengths) that are subjected to cross-metathesis with either 2-pentenenitrile or 3-pentenenitrile or unsaturated amine, resulting in unsaturated nitrile or amino acids or their esters. The produced unsaturated nitriles and esters are hydrogenated using 5 mol % Raney nickel-cobalt under a high-pressure hydrogen atmosphere. This method produces amino acids with various chain lengths. A similar method can be used for hydrocyanation of 10-decenoic acid and subsequent hydrogenation for C12 amino acid production, as well as polymerization of linear amino acids to polymers. However, the cross-metathesis yields from this method are generally low (between 13-30%), particularly when 3-pentenenitrile is used to produce nylon 12 amino acid.

There is a need for additional and improved renewable methods of producing nylons, and their precursors, that are simpler or cheaper or that involve milder reaction conditions.

SUMMARY OF THE INVENTION

Provided herein is a method of producing an amino acid or an amino ester, the method comprising subjecting oleic acid or an ester of oleic acid to a cross metathesis reaction with a coupling substrate having the formula X—$(CH_2)_n$—CH=CHY, to produce an intermediate having the formula X—$(CH_2)_n$—CH=CH—$(CH_2)_7$—COOR, wherein n=1 or 2, X=CN or OH, Y=H or $CH_2OH$, and R is either hydrogen or an alkyl group; and subjecting the intermediate to one or more reactions to convert X into an amino group to produce an amino acid or an amino ester. In certain embodiments, the one or more reactions are selected from hydrogenation, sulfonate ester formation, halogenation, and displacement of sulfonate ester or halide with ammonia. In certain embodiments, the intermediate is subjected to a hydrogenation reaction to reduce unsaturated bonds in the intermediate and produce either (i) a reduced intermediate, or (ii) an amino acid or an amino ester.

In particular embodiments, the method further includes the step of converting a hydroxyl group of the reduced intermediate into an amine to produce an amino acid or an amino ester. In particular embodiments, the step of converting a hydroxyl group into an amines comprises either sulfonate ester formation followed by displacement of the sulfonate ester, or halogenations followed by displacement of the halide.

In certain embodiments, the cross metathesis reaction is conducted in the presence of a metathesis catalyst. In certain embodiments, the metathesis catalyst comprises a tungsten-, molybdenum-, or ruthenium-based complex, or a Group 8 transition metal complex. In particular embodiments, the metathesis catalyst comprises a ruthenium-based catalyst with carbene ligands such as a second generation Hoveyda-Grubbs catalyst. In particular embodiments, the metathesis catalyst is attached to a solid support. In particular embodiments, the metathesis catalyst is continuously added over a 1-3 hour period. In particular embodiments, the metathesis catalyst is present at a catalyst loading ranging from about 0.25 mol % to about 4 mol % of oleic acid/ester. In particular embodiments, the metathesis catalyst loading is about 0.25 mol %. In particular embodiments, the metathesis catalyst loading is about 2 mol %. In certain embodiments, the metathesis catalyst loading is about 2 mol % when the coupling substrate is allyl cyanide or homoallyl cyanide, and is about 0.25 mol % when the coupling substrate is cis-butene-1,4-diol.

In particular embodiments, the metathesis catalyst is dissolved in a solvent, sometimes referred to herein for purposes of clarity as a metathesis solvent. In particular embodiments, the metathesis solvent is selected from chlorobenzene, toluene, dichloroethane, chloropentafluorobenzene, octafluorotoluene, ethyl acetate, isopropyl acetate, hexane, heptane, diethyl ether, and MTBE.

In certain embodiments, the method further comprising a step of removing the metathesis catalyst by passing the reaction mixture through silica gel. In certain embodiments, the the coupling substrate X—$(CH_2)_n$—CH=CHY is cis-butene-1,4-diol. In certain embodiments, the molar ratio of cis-butene-1,4-diol to oleic acid/ester is about 5 equivalents. In certain embodiments, the coupling substrate X—$(CH_2)_n$—CH=CHY is allyl cyanide. In certain embodiments, the molar ratio of allyl cyanide to oleic acid/ester is about five equivalents. In certain embodiments, the coupling substrate X—$(CH_2)_n$—CH=CHY is homoallyl cyanide. In certain embodiments, the molar ratio of homoallyl cyanide to oleic acid/ester is about 2.5 equivalents. In certain embodiments, the amino acid or amino ester has a formula of either $NH_2$—$(CH_2)_n$—COOR, wherein n=10-12, and R is either hydrogen or an alkyl group. In certain embodiments, the cross metathesis reaction further comprises an additive to suppress side reactions. In particular embodiments, the additive comprises 1,4-benzoquinone.

In certain embodiments, the cross metathesis reaction is conducted over a temperature range of from about −20° C. to about 130° C. In a particular embodiment, the cross metathesis reaction is conducted at a temperature of at least 0° C. In a particular embodiment, the cross metathesis reaction is conducted at a temperature of at least 95° C. In a particular embodiment, the cross metathesis reaction is conducted at a temperature of at least 110° C. In certain embodiments, the cross metathesis reaction is conducted at concentrations of oleic acid/ester ranging from about 0.025 mol/L to 0.84 mol/L. In certain embodiments, the reaction concentration of oleic acid/ester is about 0.033 mol/L. In certain embodiments, the reaction concentration of oleic acid/ester is 0.84 mol/L. In certain embodiments, the cross metathesis reaction lasts for a period of time ranging from about 2 hours to about 21 hours. In certain embodiments, the cross metathesis reaction lasts for a period of time of about 4 hours.

In certain embodiments, the hydrogenation reaction is conducted in the presence of a hydrogenation catalyst. In particular embodiments, the hydrogenation catalyst comprises palladium adsorbed on calcium carbonate support and poisoned by lead (Lindlar catalyst). In particular embodiments, the hydrogenation catalyst comprises a second generation Hoveyda-Grubbs catalyst. In particular embodiments, the hydrogenation catalyst comprises the metathesis catalyst. In particular embodiments, the hydrogenation catalyst comprises a complex of rhodium, iridium, rhenium, or ruthenium. In particular embodiments, the hydrogenation catalyst comprises a heterogeneous catalyst selected from a Raney nickel catalyst or a cobalt catalyst. In particular embodiments, the hydrogenation catalyst comprises phosphine ligands and a potassium tert-butoxide additive. In particular embodiments, the hydrogenation catalyst comprises carbene ligands. In particular embodiments, the hydrogenation catalyst is present at a catalyst loading ranging from about 1 mol % to about 6 mol % of the corresponding coupling substrate. In particular embodiments, the hydrogenation catalyst comprises a second generation Hoveyda-Grubbs catalyst present at a catalyst loading of about 2.5 mol %.

In certain embodiments, the hydrogenation reaction utilizes a hydride reducing agent. In certain embodiments, the hydrogenation reaction comprises hydrosilylation with a lewis acid. In particular embodiments, the lewis acid comprises titanium isopropoxide. In certain embodiments, the hydrogenation reaction is conducted at a temperature ranging from about 23° C. to 140° C. In certain embodiments, the hydrogenation reaction comprises dissolving the intermediate, potassium tert-butoxide, and the hydrogenation catalyst in a polar or non-polar hydrogenation solvent. In particular embodiments, the hydrogenation solvent is selected from chlorobenzene, toluene, dichloroethane, chloropentafluorobenzene, octafluorotoluene, ethyl acetate, isopropyl acetate, hexane, heptane, diethyl ether, MTBE, methanol, ethanol, and isopropanol. In particular embodiments, the hydrogenation solvent consists essentially of chlorobenzene. In particular embodiments, the potassium tert-butoxide is present in an amount ranging from about 15 mol % to about 30 mol % of the corresponding coupling substrate. In particular embodiments, the potassium tert-butoxide is present in an amount of about 30 mol %.

In certain embodiments, the hydrogenation reaction is conducted at a pressure ranging from about 20 bar to about 30 bar. In particular embodiments, the hydrogenation reaction pressure is about 25 bar. In certain embodiments, the hydrogenation reaction lasts for a period of time ranging from about 14 hours to about 40 hours. In particular embodiments, the hydrogenation reaction lasts for about 20 hours.

In certain embodiments, n in the formulas X—(CH$_2$)$_n$—CH=CHY and X—(CH$_2$)$_n$—CH=CH—(CH$_2$)$_7$—COOR is 1. In certain embodiments, n in the formulas X—(CH$_2$)$_n$—CH=CHY and X—(CH$_2$)$_n$—CH=CH—(CH$_2$)$_7$—COOR is 2. In certain embodiments, X in the formulas X—(CH$_2$)$_n$—CH=CHY and X—(CH$_2$)$_n$—CH=CH—(CH$_2$)$_7$—COOR is CN. In certain embodiments, X in the formulas X—(CH$_2$)$_n$—CH=CHY and X—(CH$_2$)$_n$—CH=CH—(CH$_2$)$_7$—COOR is OH. In certain embodiments, Y in the formula X—(CH$_2$)$_n$—CH=CHY is H. In certain embodiments, Y in the formula X—(CH$_2$)$_n$—CH=CHY is CH$_2$OH. In certain embodiments, the method further comprises a step of converting the amino acid or amino ester into a nylon compound.

In certain embodiments, the amino acid or amino ester produced is a nylon 11 precursor, a nylon 12 precursor, or a 13 precursor. In certain embodiments, the oleic acid or the ester of oleic acid is produced from algae-derived biomass. In certain embodiments, the method is implemented directly using the lipids extracted from microalgae.

Further provided are the products of the methods described herein.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIGS. 1A-1B: Schemes depicting various methods of producing nylon precursors.

FIG. 4A depicts hydrogenation following the cross-metathesis step to produce an amino ester. FIG. 4B depicts the alternative combinations of halogenation and displacement, or sulfonation and displacement, following the hydrogenation step.

FIGS. 5A-5B: Non-limiting example depicting the cross-metathesis step in a two-step method generating nylon 11, 12, and 13 precursors. (FIG. 5A.) A prior art method is also depicted for comparison. (PRIOR ART FIG. 5B.)

FIG. 7: Table 1, depicting results of the cross-metathesis of methyl-9-decenoate with allyl cyanide. Reaction conditions: to a flask containing methyl 9-decenoate (0.1 mmol), allyl cyanide (0.5 mmol), and toluene (2 mL) was added Hoveyda-Grubbs 2$^{nd}$ generation catalyst (1-2 mol %) in toluene (1 mL), dropwise over 1 h.

FIG. 8: Table 2, depicting the observed effects of polar solvents on cross-metathesis. Reaction conditions: to a flask containing methyl oleate (0.1 mmol), allyl cyanide (0.5 mmol), and 1,4-benzoquinone (0.05 mmol), in chlorobenzene (2 mL) was added Hoveyda-Grubbs 2$^{nd}$ generation catalyst (2 mol %) in chlorobenzene (1 mL), dropwise at 110° C.

FIG. 9: Table 3, depicting results of the cross-metathesis of methyl oleate with allyl cyanide. Reaction conditions: to a flask containing methyl oleate (0.1 mmol), allyl cyanide (0.5 mmol), and 1,4-benzoquinone (0.05 mmol), in chlorobenzene (2 mL) was added Hoveyda-Grubbs 2$^{nd}$ generation catalyst (2 mol %) in chlorobenzene (1 mL), dropwise at 110° C.

FIG. 10: Table 4, depicting the results of the solvent and temperature effects of cross-metathesis of methyl oleate with cis-butene-1,4-diol. Reaction conditions: to a flask containing methyl oleate (0.1 mmol) and cis-butene-1,4-diol (0.5 mmol) in ethyl acetate (1 mL) was added a catalyst dropwise (2 mol %) in ethyl acetate (1 mL) at 0° C. The reaction mixture was stirred at this temperature for more than 3 hours and warmed to room temperature with continued stirring for several additional hours.

FIG. 11: Table 5, depicting the results of the catalyst screening of cross-metathesis of methyl oleate with cis-butene-1,4-diol. Reaction conditions: to a flask containing methyl oleate (0.1 mmol) and cis-butene-1,4-diol (0.5 mmol) in ethyl acetate (1 mL) was added a catalyst dropwise (2 mol %) in ethyl acetate (1 mL) at 0° C. The reaction mixture was stirred at this temperature for more than 3 hours and warmed to room temperature with continued stirring for several additional hours.

FIG. 12: Table 6, depicting results of the hydrogenation of methyl 11-cyanoundec-9-enoate. Reaction conditions: 20 mg of methyl 11-cyano-9-undecenoate, 30 mol % of t-BuOK, 3 mol % of Grubbs 2$^{nd}$ generation catalyst, 3 mL of chlorobenzene at 80° C., 30 bars during 20 h with stirring.

FIG. 13: Table 7, depicting results of the cross-metathesis of a crude algal lipid containing a mixture of fatty acid methyl esters with either acrylonitrile or allyl cyanide. Reaction conditions: 0.1 mmol of methyl oleate, 50 mol % 1,4-benzoquinone, 2 mol % of Hoveyda-Grubbs 2$^{nd}$ generation in chlorobenzene (1 mL) added dropwise into 1.5 mL of chlorobenzene at 110° C.

DETAILED DESCRIPTION OF THE INVENTION

Figure 2A:
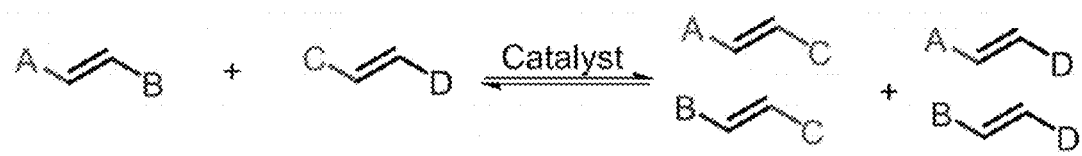
FIGS. 2A-2B: Scheme depicting olefin cross metathesis (FIG. 2A) and structures of exemplary, non-limiting olefin metathesis catalysts (FIG. 2B).

Throughout this disclosure, various publications, patents and published patent specifications are referenced by an identifying citation. The disclosures of these publications, patents, and published patent specifications are hereby incorporated by reference into the present disclosure in their entirety to more fully describe the state of the art to which this invention pertains.

Provided herein are methods for synthesizing 11-aminododecanoic-, 12-aminododecanoic-, or 13-aminotridecanoic acids, or their esters, from oleic acid or its ester, which may originate from vegetable oils or algal lipids. Oleic acid methyl ester constitutes an abundantly available feedstock, and is the main component of algal lipids. The methods involve the following general steps: (1) preparing 10-hydroxy-9-undecenoic acid, 11-cyano-9-undecenoic acid, 12-cyano-9-dodecenoic acid, or their esters, by cross-metathesis of oleic acid or its ester with either cis-butene-1,4-diol, 3-butenenitrile (allyl cyanide), or 4-pentenenitrile (homoallyl cyanide); and (2) subjecting the prepared intermediate compound to one or more further reactions to produce an amino acid or an amino ester. Step (2) generally involves hydrogenating all the unsaturation of the above intermediate molecules, and may involve converting hydroxyl groups to amino groups. In some embodiments, step (2) involves halogenation or sulfonation followed by displacement of the sulfonate ester or halide with ammonia, in order to convert hydroxyl groups present in the reduced intermediate molecules (produced from hydrogenation) into amino groups.

The methods herein allow for the direct conversion of oleic acid, an abundant natural fatty acid from vegetable oil or algae sources, into precursors of nylon 11, 12, and 13 in fewer steps than previously developed methods, and without the need for special equipment. These and other advantages over other existing strategies allow for the production of these bioplastics at competitive prices. The present disclosure provides for the ability to obtain high yields of nylon 11, 12, and 13 precursors from oleic acid methyl esters through efficient 2-4 step processes. In previous methods, the production of the nylon 11 precursor has required 4 steps from recinoleic acid, naturally available only in castor beans and castor oil as a feedstock. Those of nylon 12 precursor involved at least 5-6 steps and required the use of petroleum feedstock. Thus, previous nylon 11 and 12 synthesis methods are restricted to one feedstock (castor oil or butadiene, respectively), in addition to the large number of process steps. Nylon 13 precursor, on the other hand, has not been studied extensively except for one reported synthesis that required several steps from another unique acid available from erucic oil. The method of the present disclosure provides a shorter and simpler synthetic route for the production of nylon 11, 12, and 13 from a low-cost feedstock, oleic acid, which is abundantly available from a large variety of vegetable oils (e.g., soy or canola) as well as microalgae.

In certain embodiments, provided is a method having the following general steps: cross-metathesis, hydrogenation, and functional group conversion from oleic acid or an ester of oleic acid (such as oleic acid methyl ester). This method has several advantages over existing strategies for the production of bioplastics at competitive prices. It allows for the production of nylon 11, 12, and 13 from oleic acid, which is a low-cost fatty acid abundantly present in most common vegetable oils and algae. The feedstock is less expensive, and is non-toxic as compared to castor oil (which contains ricin). The method has a simple 2-4 process, as opposed to the 4-6 steps in currently available chemical syntheses. Also, in certain embodiments, the method only utilizes mild reaction conditions as opposed to previous methods, and requires no special equipment.

Figure 3:
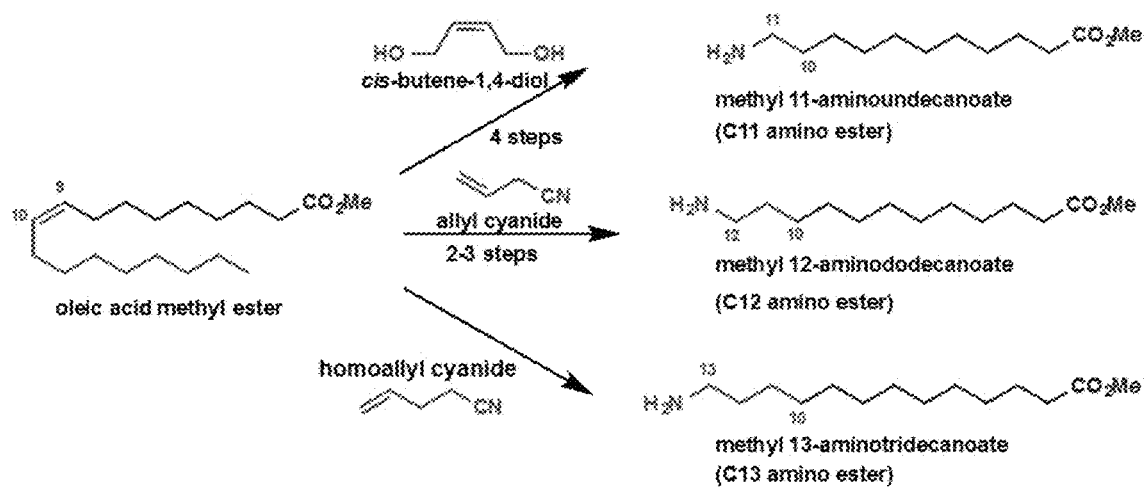
FIG. 3: Methods of converting oleic acid methyl ester into C11, C12, and C13 amino ester via cross-metathesis reactions.
Figure 4A:
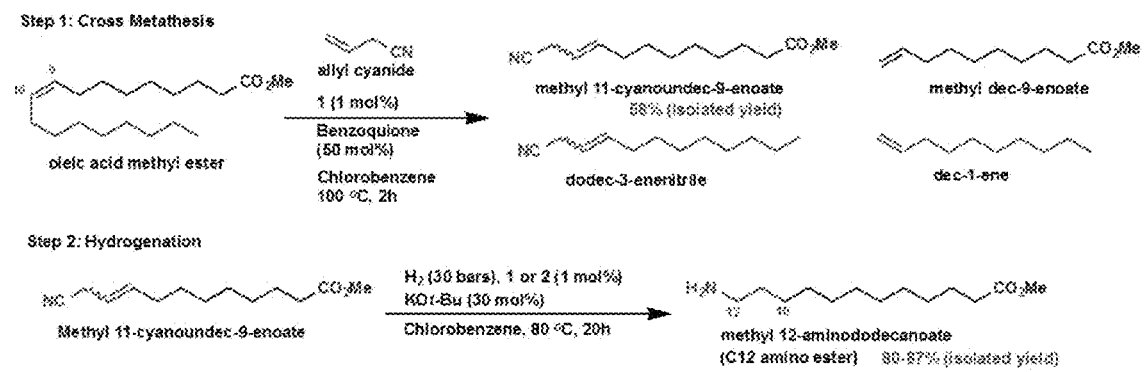
FIGS. 4A-4B: Non-limiting examples of reaction conditions for the methods depicted in FIG. 3.
Figure 4B:
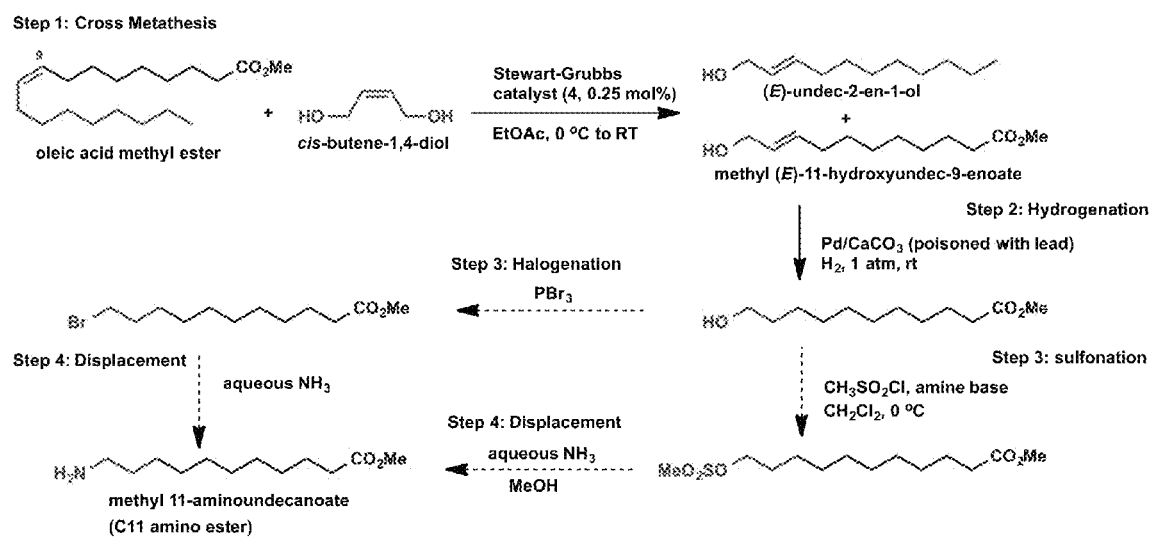
Figure 5A:
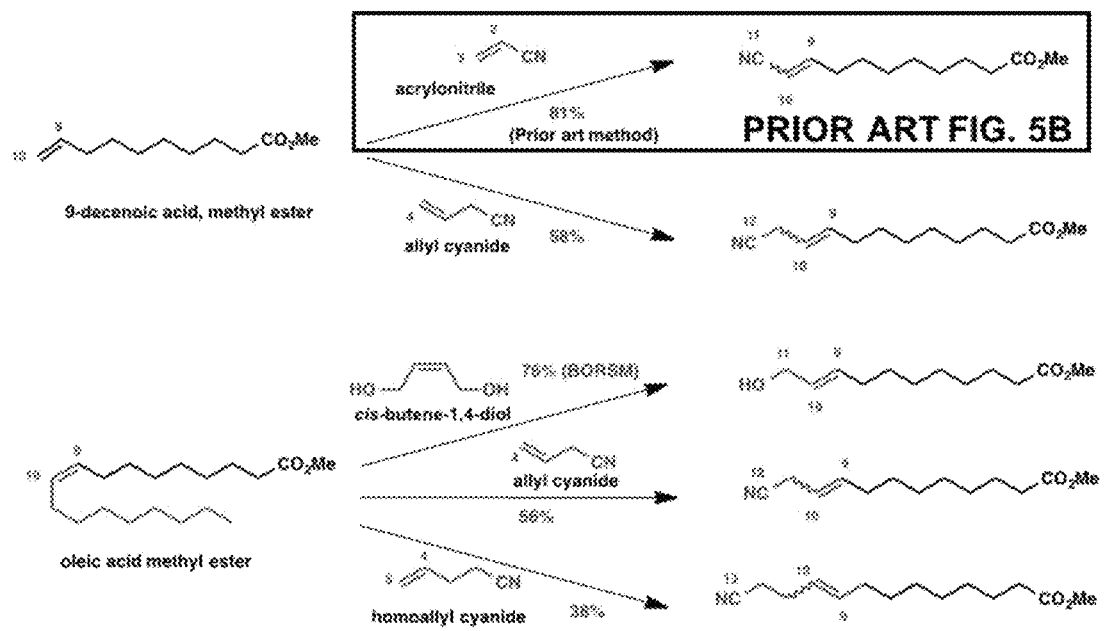

Non-limiting examples of the two-step method are depicted in FIGS. 3-5. In the first step, oleic acid or ester is subjected to cross-metathesis with alkenyl cyanide or alcohol having various chain lengths, thereby generating cyano or hydroxyl ester intermediates. Olefin cross-metathesis is a disproportionation reaction that can transfer a carbon chain to another molecule across a C=C bond in the presence of a metathesis catalyst. (FIG. 2A.) The secondary products of the metathesis are short-to-medium chain alkenes and fatty amines, which are hydrocarbon fuels and surfactants, respectively. Although up to four products can be produced in this process when, for example, oleic acid methyl ester is reacted with allyl cyanide (as shown in FIG. 4A, step 1), it is possible to tune the reaction conditions such that the reaction mainly produces the cyano ester and alkyl nitrile. A non-limiting example for the first step leading to 12-aminododecanoate is shown in FIGS. 3-4. In this example, the main products are methyl 11-cyanounec-9-enoate and dodec-3-enenitrile. (FIG. 4A, step 1.) In the second step, the intermediate molecules are subjected to hydrogenation of the double and triple bonds, thereby delivering the corresponding amino esters. (FIG. 4A, step 2.) Similarly, cross-metathesis with alkenyl alcohols can be tuned to generate only two products. A non-limiting example for this step generating 11-hydroxyundec-9-enoate and undec-2-en-1-ol is shown in FIG. 4B. In the second step, the intermediate molecules are subjected to hydrogenation of the double bonds. The rest of the sequence of converting the hydroxy groups to amino groups provides the corresponding amino esters in good overall yield without reaction optimization (FIG. 4B).

Figure 2B:
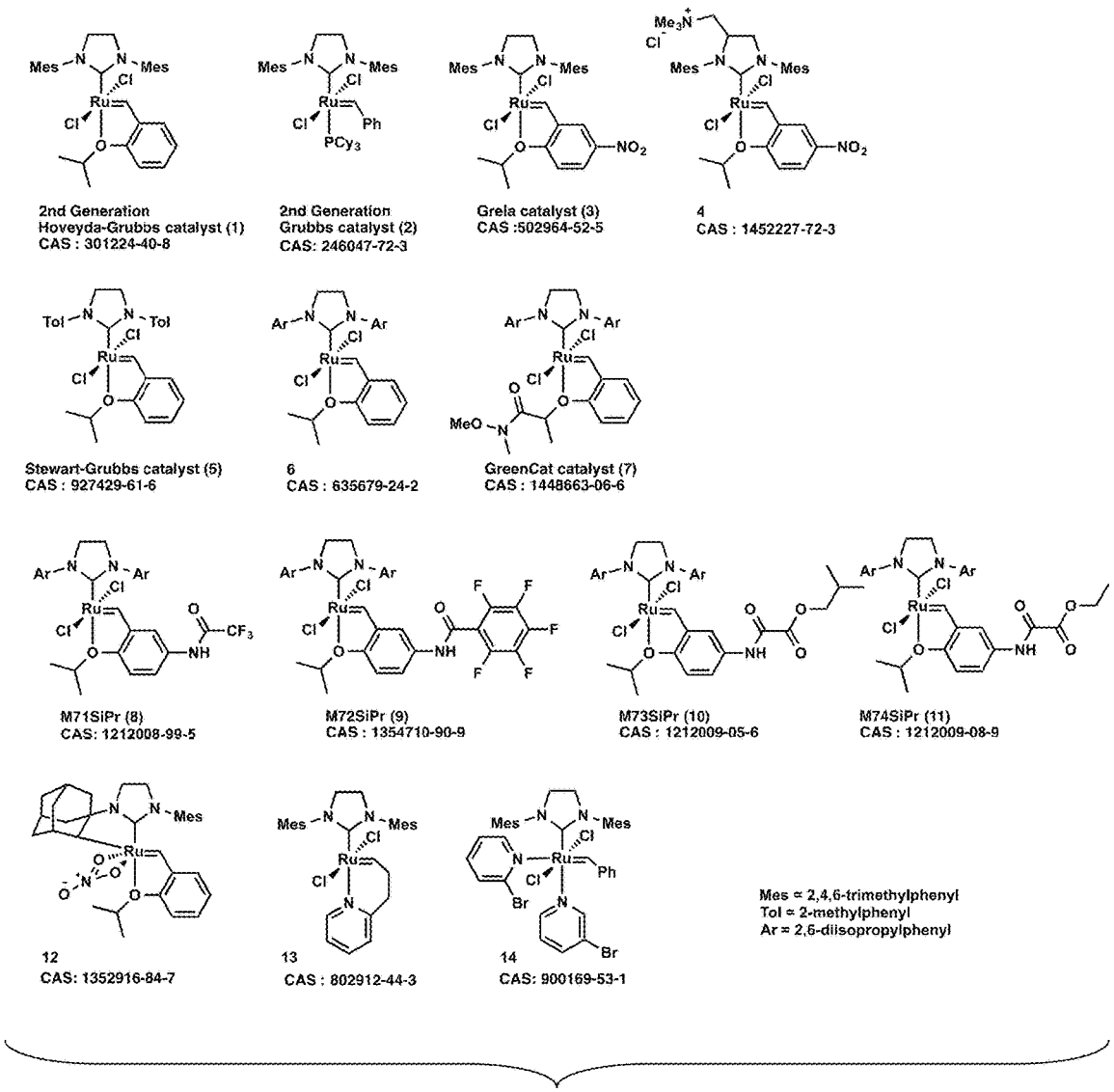

Any active catalyst can be used in the cross metathesis step of the two-step method. There are a number of catalysts commercially available for catalysis of the metathesis reaction in natural fatty acids for oleochemical production. Some suitable catalysts are tungsten-, molybdenum-, or ruthenium-based complexes. These are homogeneous catalysts, although heterogeneous catalyst adsorbed on silica or alumina are also possible. Additionally, immobilized catalysts, where the metal complex is attached to an inactive support through their ligands, can be used Immobilized catalysts are advantageous for purposes of catalyst recycling. Using an immobilized catalyst, a continuous process is possible. In particular embodiments, the catalyst used is the commercially available ruthenium complex 1 or 5 (FIG. 2B). Other possible catalysts include, but are not limited to, Group 8 transition metal complexes such as ruthenium or osmium alkylidene complexes substituted with an N-heterocyclic carbene ligand. Ruthenium and osmium carbene complexes having metal centers that are formally in the +2 oxidation state, having an electron count of 16, and that are penta-coordinated are especially useful catalysts for olefin metathesis. The skilled practitioner will recognize that any catalyst structurally similar to a Grubbs-type catalyst can be used, such as a second generation Grubbs catalyst 2 (FIG. 2B) or a second generation Hoveyda-Grubbs catalyst 1 (FIG. 2B). Any of the catalysts shown in FIG. 2B are suitable metathesis catalysts.

The catalyst can be added to the reaction medium as a solid, or as a solution wherein the catalyst is dissolved in an appropriate solvent. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction.

The two-step method shows a completely different reaction profile than previously used methods when examined using methyl 9-decenoate and allyl cyanide (FIG. 7, Table 1). Under the reaction conditions used previously (entries 1-3), while the reaction conversion is good (>92%) at reaction temperature higher than 95° C., only ~30% (by GC area) of the desired product was seen. The complex mixture of products comprised unsaturated cyano esters with various alkyl chain lengths, with molecular weight varying by 14. Without wishing to be bound by theory, it is believed this arose from olefin isomerization (see also Examples 1 and 2). Other major side-products of the reaction were a series of oligomers with structures yet to be determined. In order to suppress the undesired isomerization, the reaction was examined with several additives. One of the additives, 1,4-benzoquinone, was found to almost completely suppress the side reaction in the system (FIG. 7, Table 1, entries 4, 5, 7-14). In order to fully suppress the side reaction, 50 mol % of the additive was required (entries 12 and 14).

The olefin cross-methathesis step can be difficult to control. Therefore, the reaction parameters were screened to suppress oligomerization and to further improve the reaction conversion. A reaction temperature of at least 95° C. was required for good reaction conversion, however the reaction showed the best profile at 110° C. (FIG. 7, Table 1, entries 5 and 7). The reaction conversion was improved with a continuous injection of ruthenium catalyst over a 1-2 hour period (FIG. 7, Table 1, entries 5, 8, 11). A concentration of the reaction between 0.025-0.033 mol/L was found to provide the best balance of reaction conversion and oligomerization (FIG. 7, Table 1, entries 13 and 14). The preferred molar ratio of allyl cyanide was found to be five equivalents (FIG. 7, Table 1, entries 2, 10, 12). Optimal catalyst loading was also examined, with 2 mol % catalyst loading producing greater conversion than 1 mol % catalyst loading at the same reaction temperature (FIG. 7, Table 1, entries 4 and 5).

Solvent selection significantly influences reaction conversion and selectivity. (FIG. 8, Table 2). There are several advantages to using halogenated solvents in metathesis reactions. Table 2 shows the results of having screened halogenated and non-halogenated solvents. The use of chlorobenzene was seen to be particularly effective in the two-step process. (FIG. 8, Table 2, entry 4). However, many different metathesis solvents are possible. Suitable metathesis solvents can be polar or nonpolar and include, but are not limited to: chlorobenzene, toluene, dichloroethane, chloropentafluorobenzene, octafluorotoluene, $CH_2Cl_2$, MeOH, pentane, hexane, EtOAc, HOAc, DMSO, DMF, pyridine, water, $Et_2O$, acetonitrile, hexafluorobenzene, or mixtures thereof. In general, chlorinated and aromatic benzene derivatives, or fluorinated aromatic hydrocarbons, are suitable metathesis solvents.

The optimized cross metathesis reaction conditions for methyl 9-decenoate, determined from Tables 1 and 2, were also applicable to methyl oleate (FIG. 9, Table 3). The dimerization side reaction was suppressed using this substrate, and continuous catalyst addition was no longer needed to achieve full conversion. Thus, both 9-decenoic acid methyl ester and oleic acid methyl ester effectively underwent cross-metathesis reactions with non-conjugated nitriles as shown in in FIG. 5A.

The cross-metathesis reaction for methyl oleate and cis-butene-1,4-diol required additioinal tuning of reaction conditions. Allyl alcohol motif of the substrate generally poisons the catalyst, resulting in lower conversion under standard conditions. However, under the optimized conditions for cross-metathesis with allyl cyanide or homoallyl cyanide, which involve high temperature (110° C.) in chlorobenzene, the reaction underwent with only 9% conversion (FIG. 10, Table 4, entry 2). Surprisingly, lowering the reaction temperature strikingly improved the reaction conversion (Table 4, entries 1-8). Thus, when the reaction was performed at 0° C., reaction conversion was improved to 92% with an excellent selectivity, providing 84% yield of (E)-undece-2-en-1-ol (Table 4, entry 7-8). Since use of lower reaction temperature enabled use of other solvents, a series of more common solvents was examined (Table 4, entries 1-9). Ethyl acetate is a preferred solvent due to its low toxicity, its low cost, and its ease of removal from the product mixture.

With the optimized reaction conditions determined, other commercial ruthenium catalysts (FIG. 2B, FIG. 11, Table 5) were also examined. While most catalysts are active, none of them provided a better reaction profile than the second generation Hoveyda-Grubbs catalyst (FIG. 2B, 1), except for the Stewart-Grubbs catalyst (FIG. 2B, 5) which showed the better stability. While the Stewart-Grubbs catalyst (5) required longer reaction time to acheive full reaction conversion, the reaction profile was as clean as that of Hoveyda-Grubbs II (1) (Table 5, entries 2 vs 4). More importantly, the catalyst enabled lowering the catalyst loading from 2 mol % to 0.25 mol % without sacrificing reaction conversion and yield (Table 4, entries 8, 11, 12).

The second step, which includes hydrogenation of the olefins, is a reaction for which many catalysts are available. Hydrogenation generally involves treating an unsaturated olefin with hydrogen in the presence of a hydrogenation catalyst to produce a saturated organic compound. However, hydrogenation can also be conducted in the absence of a catalyst at high temperatures. A number of suitable hydrogenation catalysts are palladium-based, typically adsorbed on a charcoal or carbonate support, with or without additives to tune the catalyst reactivity. The reduction of nitriles to amines conventionally uses stoichiometric strong hydride reducing agents such as lithium aluminum hydride or borane, or hydrosilylation with lewis acids such as titanium isopropoxide. A more sustainable and economical hydrogenation reaction is preferred for an industrial scale process, however the reaction conditions are usually drastic, typically requiring strong heterogeneous catalysts (i.e., catalysts that are solids suspended in the solvent with the unsaturated substrate to be hydrogenated, or that are treated with gaseous substrate) such as a Raney nickel or cobalt catalyst. These catalysts only afford moderate selectivity. Catalytic hydrogenation of nitriles with a homogenous catalyst (i.e., a catalyst that can be dissolved in the solvent that contains the unsaturated substrate to be hydrogenated) has been investigated little until recently. A few examples of these catalysts are rhodium-based catalysts such as Wilkinson's catalyst, iridium-based catalysts such as Crabtree's catalyst, rhenium-based catalysts, or ruthenium-based catalysts. Of these, ruthenium complexes by far give the most selectivity and use the mildest reaction conditions.

Many hydrogenation catalytic systems use phosphine ligands and a potassium tert-butoxide additive, and are carried out between 80-140° C. under 14-75 bar pressure hydrogen atmosphere. Milder reaction conditions can be utilized when the phosphine ligands of the complex are replaced with carbene ligands. Additionally, it is possible to use the metathesis catalyst as a precursor of the metathesis reaction for the synthesis of amino acids or esters for nylon production. Therefore, any second generation Grubbs-type catalyst, such as the complexes 1 or 2 (FIG. 2B), can be used as the hydrogenation catalyst.

As with the methasis step, many different solvents are possible for use in the hydrogenation step. Suitable hydrogenation solvents include, but are not limited to: chlorobenzene, toluene, dichloroethane, chloropentafluorobenzene, octafluorotoluene, $CH_2Cl_2$, MeOH, pentane, hexane, hepane, HOAc, EtOAc, i-PrOAc, DMSO, DMF, pyridine, water, $Et_2O$, acetonitrile, hexafluorobenzene, chloroform, cyclohexane, ethyl ether, or mixtures thereof.

Figure 6:
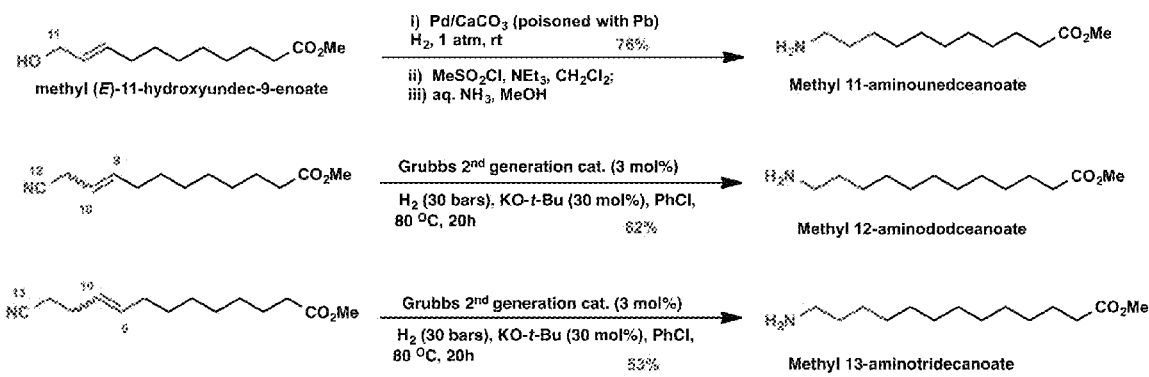
FIG. 6: Non-limiting example depicting the hydrogenation step in 2-4 step methods generating nylon 11, 12, and 13 precursors.
Figures 14A, 14B, 14C:
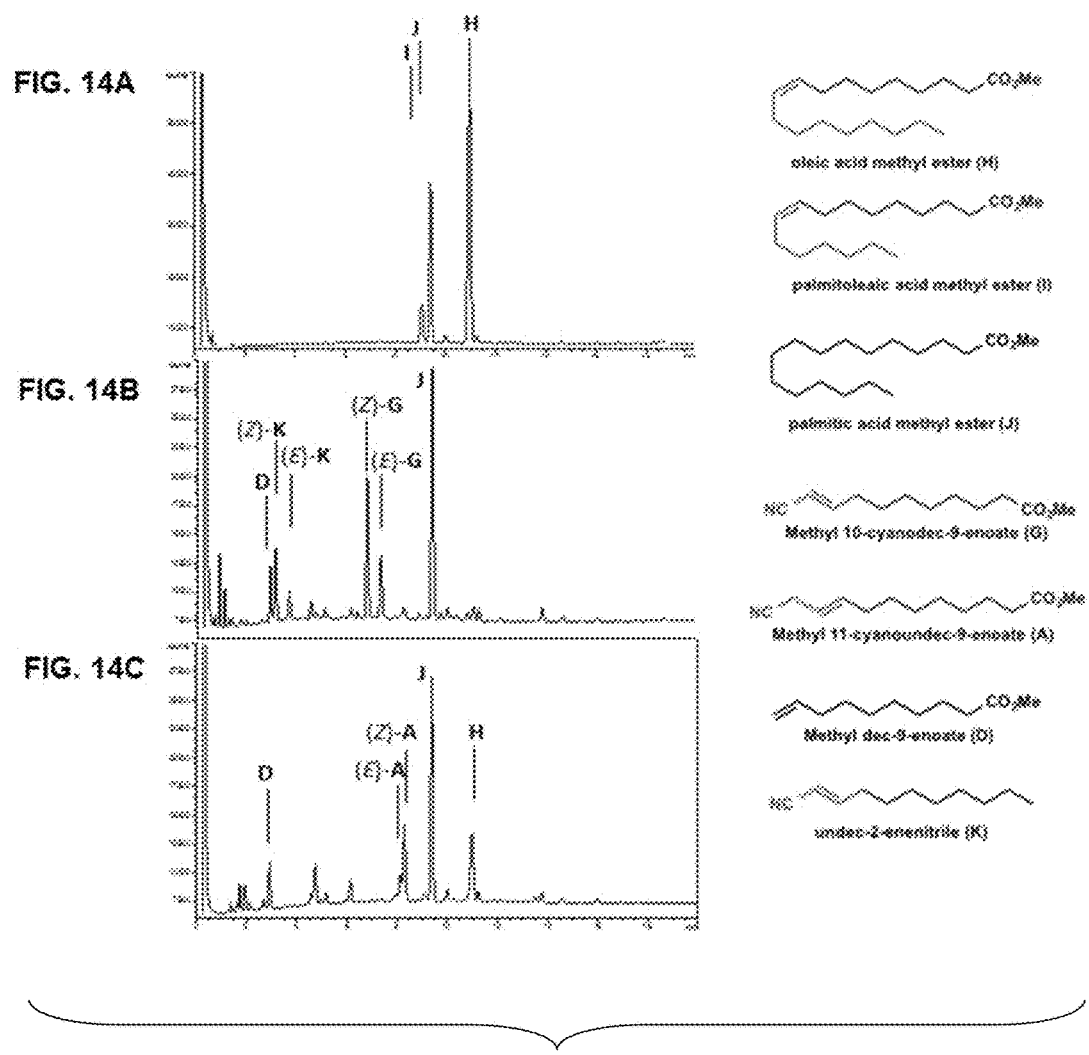
FIGS. 14A-14C: GC Chromatograms of a crude algal lipid containing a mixture of fatty acid methyl esters (FIG. 14A), cross-metathesis with acrylonitrile (FIG. 14B), and cross-metathesis with allyl cyanide (FIG. 14C).

In the examples herein, the hydrogenation reaction of 11-hydroxyundec-9-enoate was carried out using a conventional palladium-based catalyst, palladium on charcoal with a lead additive (Lindlar catalyst), under atmospheric pressure of hydrogen to provide saturated product in excellent yield (FIG. 6). The hydrogenation reactions of the substrates containing nitriles, 11-cyanoundec-9-enoate and 12-cyanododec-9-enoate, were carried out using either the catalyst 1 or 2 (FIG. 2B). Toluene, benzene, or chlorobenzene were found to be suitable solvents. As seen from Table 6, a hydrogenation reaction temperature of 80° C. provided the best overall conversion and selectivity (FIG. 12, Table 6). The base additive was found to be important in this catalyst system, and typically 30 mol % of potassium tert-butoxide was used in the process, though other additives are possible. The reaction mixture was kept for 24 hours under hydrogen pressure in between 25-30 bar. These reaction conditions provided 62% yield of the C12 amino ester, the precursor for nylon 12 (FIG. 6). The same reaction conditions were applicable to hydrogenate C13 amino ester also in 53% yield.

While the starting material, oleic acid, can be supplied economically from many renewable resources, the method herein is particularly useful if a crude lipid extracted from microalgae is directly used. Thus, the cross-metathesis reaction was tested using a mixture of fatty acid methyl esters obtained from algal biomass by a reactive-extraction technology which enables recovery of algal lipids as FAMEs in a single step. Both cross-metathesis with acrylonitrile and allyl cyanide proceeded smoothly, consuming only unsaturated FAMEs and leaving the saturated FAMEs behind (FIG. 13, Table 6, and FIGS. 14A-14C). Even under un-optimized conditions, both reactions—with acrylonitrile (Table 6, entry 1) and with allyl cyanide (Table 6, entry 2)—provided the desired cyano esters in close to comparable conversion but lower selectivity to the corresponding control reactions (acrylonitrile: Table 6, entry 3; allyl cyanide FIG. 9, Table 3, entry 6). This is the first example of cross-metathesis using crude algal lipid. It should be noted that throughput from use of crude algal lipid would be greater if applied to biomass that has a higher content of C9-unsaturated lipids.

Nylon polymers can be produced from the nylon precursors generated from the two-step method through any effective polymerization process. By way of non-limiting examples, either a batch autoclave (or discontinuous) method, or a continuous polymerization (CP) method could be utilized to produce nylon polymers. In one non-limiting example of a conventional batch autoclave method, a 40-60% amino acid salt solution is charged into a pre-evaporator vessel operated at a temperature of about 130-160° C. and a pressure of about 240-690 kPa absolute, wherein the polyamide salt solution is concentrated to about 70-80%. This concentrated solution is transferred to the autoclave, where heating is continued as the pressure in the vessel rises to anywhere from about 1100 kPA to about 4000 kPa absolute. Steam is vented until the batch temperature reaches about 220-260° C. The pressure is then reduced slowly (over about 60-90 minutes) to less than about 100 kPa absolute. The polymer molecular weight is controlled by the hold time and pressure at this stage. Salt concentration, pressure, and temperature may vary depending on the specific polyamide being processed. After the desired hold time, the polyamide is then extruded into a strand, cooled, and cut into pellets (also known as granulates).

Continuous polymerization (CP) processes are also suitable methods of preparing nylons. In one non-limiting example of a continuous polymerization method, an amino acid (or polyamide) salt solution is preheated in a vessel to about 40-90° C. and transferred into a pre-evaporator/reactor, where the salt solution is concentrated at about 1350-2000 kPa absolute and about 200-260° C. to about 70-90%, resulting in a low molecular weight polymer. The low molecular weight polymer is then discharged into a flasher, where the pressure is slowly reduced to below about 100 kPa absolute and discharged into a vessel maintained below atmospheric pressure and at a temperature of about 270-300° C., to effect removal of water and to promote a further molecular weight increase. The polyamide melt is then extruded into a strand, cooled, and cut into pellets. Though a batch autoclave and CP method are described, the skilled person will recognize that any suitable method of preparing a nylon polymer is entirely within the scope of the present disclosure and can be readily utilized to prepare nylon polymers from the nylon precursors produced by the method described herein.

The method of the present disclosure can be used to produce algae-based high-value nylons in an alternative to petroleum-derived products. The method can utilize microalgal feedstocks, which have a short growth cycle, higher surface productivity than terrestrial plants, high lipid content, and an ability to grow on wastewater systems. Microalgae is also less toxic than castor oil (which contains ricin). Nylons such as nylon 11, 12, and 13 possess excellent chemical resistance, good durability, flexibility, cold impact resistance, and thermal resistance. These products have many industrial applications in the automotive, sports, and medical industries, and are also useful for various products such as, but not limited to, high-performance cables, electronics, anti-termite cable sheathing, oil and gas flexible pipes, electrical compounds, sports shoes, catheters, control fluid umbilicals, pneumatic airbrake tubing, fuel lines, and lenses for glasses.

EXAMPLES

Example 1

Cross Methathesis with Acrylonitrile

This example illustrates the cross-metathesis step between oleic acid and acrylonitrile using previously reported reaction conditions. This reaction performed the best when carried out with the continuous addition of the metathesis catalyst.

29.7 mg of oleic acid methyl ester (0.1 mmol), acrylonitrile (35 μL, 0.534 mmol) and 1 mL of dry toluene were placed in a round bottom flask. A $2^{nd}$ Generation Grubbs-Hoveyda catalyst (0.8 mg, 0.0013 mmol) was dissolved in dry toluene (1 mL) and transferred to a syringe. An additional 1 mL of toluene was used to rinse the vial. The catalyst solution was transferred to the reaction mixture using a syringe pump, over a period of 1 h under nitrogen atmosphere with magnetic stirring (400 rpm) at 95° C. At the end of the addition, the mixture was left to react for 1.5 h at 95° C. The reaction mixture was analyzed by gas chromatography, indicating the conversion being >99% by area. GC analysis showed the four major peaks, methyl 10-cyano-9-decenoate and 2-undecenitrile (both as mixtures of E and Z isomers). The mixture was passed through a plug of silica gel (0.5 cm in Pasteur pipette) with hexane/ethyl acetate (7/3) in order to remove the catalyst, concentrated, and the residue was purified by silica gel chromatography, yielding (E)-10-cyano-9-decenoate (4.69 mg, 0.022 mmol, 22%), (Z)-10-cyano-9-decenoate (12.3 mg, 0.059 mmol, 59%), (E)-2-undecenitrile (4.76 mg, 0.029 mmol), and (Z)-2-undecenitrile (11.5 mg, 0.070 mmol) all as clear oil.

Example 2

Cross Metathesis of Methyl 9-Decenoate and Allyl Cyanide Without Benzoquinone

Methyl 9-decenoate (0.1 mmol) was added into a dry three-necked round bottom flask. The flask was purged for 10 min with nitrogen. Toluene (1 mL) was then added into the flask with a syringe followed by allyl cyanide (0.044 mL, 0.5 mmol). A $2^{nd}$ Generation Hoveyda-Grubbs catalyst (1 mol %, 0.7 mg, 0.005 mmol) was dissolved in toluene (1 mL) and transferred into a vial via syringe. 1 mL of solvent was used to rinse the vial. The solution containing the catalyst was transferred to the reaction mixture over 8 h while heating at 95° C. with stirring (400 rpm). After the completion of the addition, the reaction mixture was kept at this temperature for an additional 10 min before being cooled to room temperature.

The mixture was passed through a plug of silica gel (0.5 cm in Pasteur pipette) with hexane/ethyl acetate (7/3) in order to remove the catalyst. The product was concentrated under reduced pressure and analyzed by GC, MS, and NMR. Many by-products were identified, such as oligomer of 9-decenoate and many cyano esters with various shorter carbon chain lengths. Without wishing to be bound by theory, it is believe these arose from olefin isomerization of the desired product and/or allyl cyanide prior to the metathesis reaction.

Example 3

Cross Metathesis of Methyl-9-Decenoate and Allyl Cyanide With Benzoquinone

Methyl 9-decenoate (0.5322 mmol) was added into a dry three-necked round bottom flask. Chlorobenzene (5 mL) was then added into the flask with a syringe followed by allyl cyanide (0.220 mL, 2.735 mmol). 1,4-Benzoquinone (28.5 mg, 0.2637 mmol, 50 mol %) was dissolved in chlorobenzene (2.5 mL) and transferred to the reaction mixture by a syringe. The flask containing the mixture was purged for 10 min with nitrogen, and then heated at 110° C. with stirring (400 rpm) for 20 min. The $2^{nd}$ Generation Hoveyda-Grubbs catalyst (4.5 mol %, 15.0 mg, 0.02395 mmol) was dissolved in chlorobenzene (5 mL) and transferred into a syringe. The solution containing the catalyst was transferred to the reaction mixture drop wise over a period of 2 h while keeping the reaction temperature at 110° C. with stirring (400 rpm). After completion of the addition, the reaction mixture was kept at this temperature for an additional 1 h before being cooled to room temperature.

The mixture was passed through a plug of silica gel (0.5 cm in Pasteur pipette) with hexane/ethyl acetate (7/3) in order to remove the catalyst and concentrated. The crude product was purified by column chromatography using hexane/ethyl acetate (7/3) as an eluent, and the product was concentrated under reduced pressure to provide the desired compound as a brown oil (69.2 mg, 58%).

Example 4

Cross Metathesis of Methyl Oleate and Allyl Cyanide With Benzoquinone

Methyl oleate (0.1069 mmol) was added into a dry three-necked round bottom flask. Chlorobenzene (1 mL) was then added into the flask with a syringe followed by allyl cyanide (0.044 mL, 0.5470 mmol). 1,4-Benzoquinone (5.7 mg, 0.0527 mmol, 50 mol %) was dissolved in chlorobenzene (0.5 mL) and transferred to the reaction mixture by a syringe. The flask containing the mixture was purged for 10 min with nitrogen, and then heated at 110° C. with stirring (400 rpm) for 20 min. The $2^{nd}$ Generation Hoveyda-Grubbs catalyst (4.5 mol %, 3.0 mg, 0.0048 mmol) was dissolved in chlorobenzene (1 mL) and transferred into a syringe. The solution containing the catalyst was transferred to the reaction mixture drop wise over a period of 2 h while keeping the reaction temperature at 110° C. with stirring (400 rpm). After the completion of the addition, the reaction mixture was kept at this temperature for an additional 1 h before being cooled to room temperature.

The mixture was passed through a plug of silica gel (0.5 cm in Pasteur pipette) with hexane/ethyl acetate (7/3) in order to remove the catalyst, and a small sample was then analyzed by GC, which showed the reaction completion (56% GC yield of the desired product). The main by-products were the dimer of allyl cyanide and the dimer of methyl oleate.

Example 5

Cross Metathesis With Homoallyl Cyanide With Benzoquinone

Methyl oleate (1.0547 mmol) was added into a dry three-necked round bottom flask. Chlorobenzene (10 mL) was then charged into the flask with a syringe followed by 4-pentenenitrile (0.530 mL, 5.488 mmol). 1,4-Benzoquinone (57.8 mg, 0.5347 mmol, 50 mol %) was dissolved in chlorobenzene (5 mL) and transferred to the reaction mixture by a syringe. The flask containing the mixture was purged for 10 min with nitrogen, and then heated at 110° C. with stirring (400 rpm) for 20 min. The $2^{nd}$ Generation Hoveyda-Grubbs catalyst (4.5 mol %, 29.7 mg, 0.00474 mmol) was dissolved in chlorobenzene (1 mL) and transferred into a syringe. The solution containing the catalyst was transferred to the reaction mixture drop wise over a period of 2 h while keeping the reaction temperature at 110° C. After completion of the addition, the reaction was kept at this temperature for additional 1 h before being cooled to room temperature.

The crude product was purified by column chromatography using hexane/ethylacetate (9/1) as an eluent, and concentrated under reduced pressure to provide the desired compound as a reddish brown oil (94.7 mg, 38%).

Example 6

High-Pressure Hydrogenation of 12-Cyano-9-dodecenoic Acid Methyl Ester

12-Cyano-9-dodecenoic acid methyl ester (20.1 mg, 0.0901 mmol) and t-BuOK (33.64 mol %, 3.4 mg, 0.0303 mmol) were charged in a 2-dram vial and dissolved in 2 mL of chlorobenzene. $2^{nd}$ generation Hoveyda-Grubbs catalyst (2.5 mol %, 1.4 mg, 0.0022 mmol) was dissolved in chlorobenzene (1 mL) and transferred into the vial. The vial was placed in a Parr reactor which was purged 3 times with hydrogen gas before being pressurized at 30 bars and heated at 80° C. with stirring for 20 h. Subsequently, the reaction mixture was purified by silica gel chromatography using hexane/methanol/DCM (8/1/1) as an eluent, and concentrated under reduced pressure to give methyl 12-aminododecanoate (19 mg, 87%).

Example 7

Cross Metathesis of Methyl Oleate and cis-1,4-Butenediol

Methyl oleate (250 mg, 0.84 mmol) and cis-2-butene-1, 4-diol (374.2 mg, 4.2474 mmol) were taken to a 25-mL three neck flask. The mixture was stirred at 0° C. in an ice bath under argon atmosphere. After 20 mins, solution of dichloro[1,3-bis(2-methylphenyl)-2-imidazolidinylidene](2-isopropoxyphenylmethylene)ruthenium(II) (1.2 mg, 0.002 mmol; Stewart-Grubbs catalyst (5)) in 1.0 mL ethyl acetate) was added drop-wise over 1 h using a syringe pump. After 6 h at 0° C., the reaction mixture was warmed to room temperature with continuous stirring. The reaction mixture was passed through a small plug of silica gel. An additional 2.0 mL of ethyl acetate was used to flush the silica gel plug. The filtrate was concentrated and purified by silica gel flash column chromatography (ethyl acetate:hexane, 1:9→1:4). The desired product was obtained as a clear colorless liquid (114 mg, 76% BORSM). 41 mg of unreacted starting material was recovered.

Example 8

Hydrogenation of 11-Hydroxy-9-undecenoic Acid Methyl Ester

A suspension of 5% Pd/CaCO$_3$ (50 mg, poisoned with lead) in 1.0 mL of ethanol was purged with hydrogen gas using a hydrogen balloon for 15 min. Methyl (E)-11-hydroxyundec-9-enoate (100 mg, 0.47 mmol) dissolved in 2 mL of ethanol was added and stirred at room temperature under hydrogen atmosphere for 14 h. The reaction mixture was passed through a pad of Celite® and concentrated using a rotary evaporator. (79 mg, 78% GC yield, corrected).

Certain embodiments of the methods and products disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:
1. A method of producing an amino acid or an amino ester, the method comprising:
subjecting oleic acid or an ester of oleic acid to a cross-metathesis reaction with a coupling substrate of formula X—(CH$_2$)$_n$—CH=CHY, to produce an intermediate of formula X—(CH$_2$)$_n$—CH=CH—(CH$_2$)$_7$—COOR, wherein n=1 or 2, X=OH or CN, Y=H or CH$_2$OH, and R is either hydrogen or an alkyl group;
subjecting the intermediate to one or more reactions to convert X into an amino group, to produce an amino acid or an amino ester; wherein the intermediate is subjected to a hydrogenation reaction to reduce unsaturated bonds in the intermediate and produce either (i) a reduced intermediate, or (ii) an amino acid or an amino ester; and,
converting a hydroxyl group of the reduced intermediate into an amine to produce an amino acid or an amino ester; wherein the step of converting a hydroxyl group into an amine comprises either sulfonate ester formation followed by displacement of the sulfonate ester with ammonia, or halogenation followed by displacement of the halide with ammonia.

2. The method of claim 1, wherein the cross-metathesis reaction is conducted in the presence of a metathesis catalyst.

3. The method of claim 2, wherein the metathesis catalysts comprises a tungsten-, molybdenum-, or ruthenium-based complex, or a Group 8 transition metal complex.

4. The method of claim 2, wherein the metathesis catalyst comprises a second generation Hoveyda-Grubbs catalyst.

5. The method of claim 2, wherein the metathesis catalyst is attached to a solid support.

6. The method of claim 2, wherein the metathesis catalyst is present at a catalyst loading ranging from about 0.25 mol% to about 4 mol% of the coupling substrate.

7. The method of claim 2, wherein the metathesis catalyst is dissolved in a metathesis solvent selected from the group consisting of chlorobenzene, toluene, dichloroethane, chloropentafluorobenzene, octafluorotoluene, ethyl acetate, isopropyl acetate, hexane, heptane, diethyl ether, and MTBE.

8. A method of producing an amino acid or an amino ester, the method comprising:
subjecting oleic acid or an ester of oleic acid to a cross-metathesis reaction with a coupling substrate of formula X—(CH2)n—CH=CHY, to produce an intermediate of formula X—(CH2)n—CH=CH—(CH2)7—COOR, wherein n=1 or 2, X=OH or CN, Y=H or CH2OH, and R is either hydrogen or an alkyl group; and
subjecting the intermediate to one or more reactions to convert X into an amino group, to produce an amino acid or an amino ester;
wherein the coupling substrate of formula X—(CH$_2$)$_n$—CH=CHY is cis-butene-1,4-diol (HO—CH$_2$—CH=CH—CH$_2$—OH), and the resulting amino acid or amino ester is nylon 11 precursor.

9. The method of claim 8, wherein the molar ratio of the cis-butenen-1,4-diol to the oleic acid or the ester of oleic acid is about five equivalents.

10. The method of claim 1, wherein the coupling substrate of formula X—(CH$_2$)$_n$—CH=CHY is allyl cyanide (NC—CH$_2$—CH=CH$_2$), and the resulting amino acid or amino ester is nylon 12 precursor.

11. The method of claim 10, wherein the molar ratio of the allyl cyanide to the oleic acid or the ester of oleic acid is about five equivalents.

12. The method of claim 1, wherein the coupling substrate of formula X—(CH$_2$)$_n$—CH=CHY is homoallyl cyanide (NC—(CH$_2$)$_2$—CH=CH$_2$), and the resulting amion acid or amino ester is nylon 13 precursor.

13. The method of claim 12, wherein the molar ratio of the homoallyl cyanide to the oleic acid or the ester of oleic acid is about 2.5 equivalents.

14. The method of claim 1, wherein the cross-metathesis reaction is conducted in the presence of an additive selected from the group consisting of: 1,4-benzoquinone; 2,3-dichloro-1,4-benzoquinone; 2,3-difluoro-1,4-benzoquinone; and 2,3,5,6-tetrafluoro- 1,4-benzoquinone.

15. A method of producing an amino acid or an amino ester, the method comprising:
subjecting oleic acid or an ester of oleic acid to a cross-metathesis reaction with a coupling substrate of formula X—(CH2)n—CH=CHY, to produce an intermediate of formula X—(CH2)n-CH =CH—(CH2)7—COOR, wherein n=1 or 2, X=OH or CN, Y=H or CH2OH, and R is either hydrogen or an alkyl group; and subjecting the intermediate to one or more reactions to convert X into an amino group, to produce an amino acid or an amino ester;
wherein the cross-metathesis reaction is conducted with cis-butene-1,4-diol, at a temperature ranging from about −10 °C. to about 5 °C.

16. The method of claim 1, wherein the cross-metathesis reaction is conducted with allyl cyanide at a temperature ranging from about 95 °C. to about 110 °C.

17. The method of claim 1, wherein the cross-metathesis reaction is conducted with homoallyl cyanide at a temperature ranging from about 95 °C. to 110 °C.

18. The method of claim 1, wherein the cross-metathesis reaction is conducted at a concentration of the oleic acid or the ester of oleic acid ranging from about 0.025 mol/L to about 0.84 mol/L.

19. The method of claim 1, wherein the cross-metathesis reaction lasts for a time period ranging from about 2 hours to about 21 hours.

20. The method of claim 1, wherein the hydrogenation reaction is conducted in the presence of a hydrogenation catalyst selected from the group consisting of: palladium adsorbed on a support, with or without an additive; and a complex of rhodium iridium, rhenium, or ruthenium and carbene ligands.

21. The method of claim 20, wherein the hydrogenation catalyst is present at a catalyst loading ranging from about 1 mol % to 6 mol % of the coupling substrate.

22. The method of claim 20, wherein the hydrogenation catalyst comprises a potassium or sodium tert-butoxide additive at a loading of 15-30 mol % of the coupling substrate.

23. The method of claim 20, wherein the hydrogenation reaction comprises dissolving the intermediate, sodium or potassium tert-butoxide, and the hydrogenation catalyst in a polar or non-polar hydrogenation solvent selected from the group consisting of chlorobenzene, toluene, dichloroethane, chloropentafluorobenzene, octafluorotoluene, ethyl acetate, isopropyl acetate, hexane, heptane, diethyl ether, MTBE, methanol, ethanol, and isopropanol.

24. The method of claim 1, wherein the oleic acid or the ester of oleic acid is produced from algae-derived biomass.

* * * * *